US009303021B2

(12) United States Patent  
Donello et al.

(10) Patent No.: US 9,303,021 B2
(45) Date of Patent: Apr. 5, 2016

(54) METHODS FOR TREATING COGNITIVE DISORDERS USING 3-ARYL-3-HYDROXY-2-AMINO-PROPIONIC ACID AMIDES, 3-HETEROARYL-3-HYDROXY-2-AMINO-PROPIONIC ACID AMIDES AND RELATED COMPOUNDS

(71) Applicant: Allergan, Inc., Irvine, CA (US)

(72) Inventors: John E. Donello, San Clemente, CA (US); Fabien J. Schweighoffer, Val-de-marne (FR); Lauren M. Luhrs, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/218,501

(22) Filed: Mar. 18, 2014

(65) Prior Publication Data

US 2014/0296287 A1  Oct. 2, 2014

Related U.S. Application Data

(63) Continuation of application No. 14/133,131, filed on Dec. 18, 2013, now abandoned, which is a continuation of application No. 12/530,124, filed as application No. PCT/US2008/055812 on Mar. 4, 2008, now Pat. No. 8,623,891.

(60) Provisional application No. 60/893,196, filed on Mar. 6, 2007.

(51) Int. Cl.
| C07D 409/06 | (2006.01) |
| C07D 333/22 | (2006.01) |
| C07D 213/50 | (2006.01) |
| A61K 31/44 | (2006.01) |
| C07D 215/14 | (2006.01) |
| C07D 295/192 | (2006.01) |
| C07D 307/52 | (2006.01) |
| C07D 401/06 | (2006.01) |
| C07D 405/06 | (2006.01) |

(52) U.S. Cl.
CPC ............ *C07D 409/06* (2013.01); *C07D 213/50* (2013.01); *C07D 215/14* (2013.01); *C07D 295/192* (2013.01); *C07D 307/52* (2013.01); *C07D 333/22* (2013.01); *C07D 401/06* (2013.01); *C07D 405/06* (2013.01)

(58) Field of Classification Search
CPC ... C07D 409/06; C07D 333/22; C07D 213/30
USPC ................. 514/209, 305–307, 299
See application file for complete search history.

(56) References Cited

U.S. PATENT DOCUMENTS

| 5,945,442 | A | 8/1999 | Shayman et al. |
| 5,952,370 | A | 9/1999 | Shayman et al. |
| 6,030,995 | A | 2/2000 | Shayman et al. |
| 6,051,598 | A | 4/2000 | Shayman et al. |
| 2002/0115667 | A1 | 8/2002 | Walkley et al. |
| 2003/0050299 | A1 | 3/2003 | Hirth et al. |
| 2003/0153768 | A1 | 8/2003 | Hirth |

FOREIGN PATENT DOCUMENTS

| WO | 00-62780 | 10/2000 |
| WO | 01-38228 | 5/2001 |
| WO | 03008399 A | 1/2003 |
| WO | 2006-081252 A2 | 8/2006 |
| WO | 2006-081276 A1 | 8/2006 |
| WO | 2006-0812820 A1 | 8/2006 |
| WO | 2006081273 A | 8/2006 |

OTHER PUBLICATIONS

Kastron et al., Latvijas PSR Zinatnu Akademijas Vestis, Kimijas Serija, 1965, 474-477, 4.
Kurosawa et al., C-Labelling of a Novel Atypical B-Adrenoceptor Agonist, SM-11044, Journal of Labelled Compounds & radiopharmaceuticals, Mar. 1996, 285-297, 38-3, John Wiley & Sons, Ltd.
Shin, Seong-Ho et al, Stereoselective Synthesis of Enantiomerically Pure D-Threo-PDMP; Manipulation of Core 2,3-Diamino alchohol Unit, Tetrahedron: Asymmetry, 2000, 3293-3301, 11.
Patent Cooperation Treaty, Notification of Transmittal of the International Search Report and the Written Opinion of the International Authority, of the Declaration, PCT Application No. PCT/US2008/055812, mailed Sep. 7, 2008.
Yamagishi et al., A synthetic Ceramide Analog Ameliorates Spatial Cognition Deficit and Stimulates Biosynthesis of Brain Gangliosides in Rats with Cerebral Ischemia, European Journal of Pharmacology, vol. 462, No. 1-3, Feb. 21, 2003, pp. 53-60.
Schneider et al., The Synthetic Ceramide Analog 1-PDMP Partially Protects Striatal Dopamine Levels but does not Promote Dopamine Neuron Survival in Murine Models of Parkinsonism, Brain Research, vol. 1099, No. 1, Jul. 12, 2006, pp. 199-205.

*Primary Examiner* — San-Ming Hui
(74) *Attorney, Agent, or Firm* — Jonathan Bass

(57) ABSTRACT

Disclosed herein are methods of treating a patient suffering from a cognitive disorder using compounds of Formulas 1 and 2

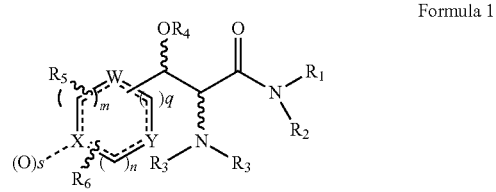

Formula 1

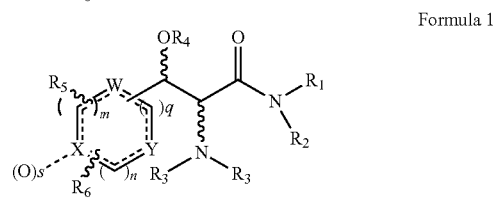

Formula 1 wherein the variables have the meaning disclosed in the specification.

11 Claims, No Drawings

METHODS FOR TREATING COGNITIVE DISORDERS USING 3-ARYL-3-HYDROXY-2-AMINO-PROPIONIC ACID AMIDES, 3-HETEROARYL-3-HYDROXY-2-AMINO-PROPIONIC ACID AMIDES AND RELATED COMPOUNDS

CROSS REFERENCE TO RELATED APPLICATIONS

This patent application is a continuation of U.S. patent application Ser. No. 14/133,131, filed on Dec. 18, 2013 which is a continuation of U.S. patent application Ser. No. 12/530,124, filed on Sep. 4, 2009, which is national stage application under 35 U.S.C. §371 of PCT patent application PCT/US2008/055812, filed on Mar. 4, 2008 which claims the benefit of U.S. Provisional Application No. 60/893,196, filed Mar. 6, 2007, and which is incorporated herein by reference.

BACKGROUND OF THE INVENTION

The present invention is directed to methods of treating a patient suffering from one or more types of cognitive disorders using derivatives of 3-aryl-3-hydroxy-2-amino-propionic acid amides, 3-heteroaryl-3-hydroxy-2-amino-propionic acid amides, and related compounds.

Several compounds falling within one or more of the general definitions as "derivatives of 3-aryl-3-hydroxy-2-amino-propionic acid amides, of 3-heteroaryl-3-hydroxy-2-amino-propionic acid amides, of 1-aryl-1-hydroxy-2,3-diamino-propyl amines, 1-heteroaryl-1-hydroxy-2,3-diamino-propyl amines" are known in the patent and scientific literature. For example, United States Patent Application Publication Nos. 2003/0153768 and 2003/0050299 disclose several examples of the above-mentioned known compounds. Illustrative specific examples of compounds of these references are shown below:

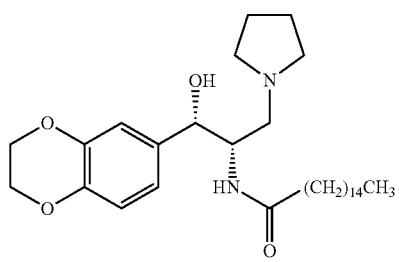

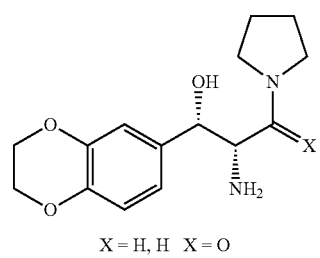

X = H, H  X = O

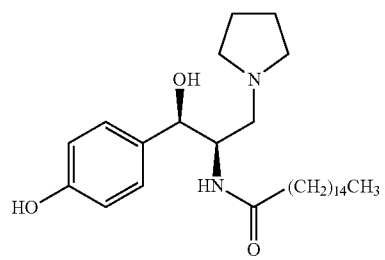

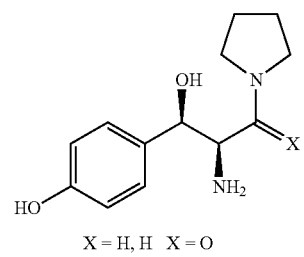

X = H, H  X = O

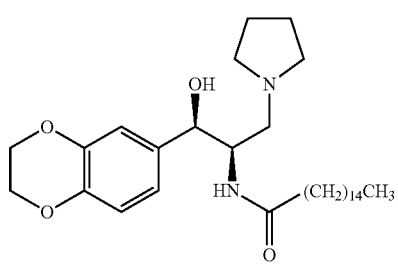

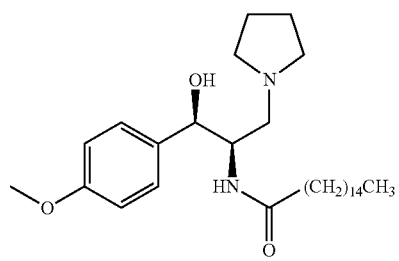

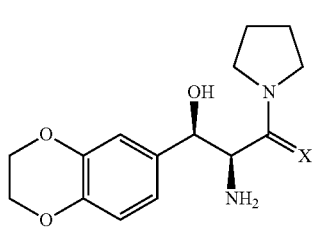

X = H, H  X = O

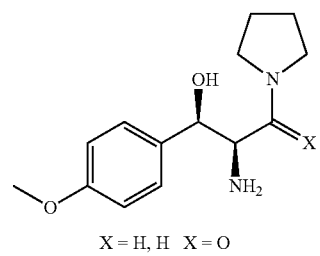

X = H, H  X = O

The publication Shin et al. *Tetrahedron Asymmetry*, 2000, 11, 3293-3301 discloses the following compounds:

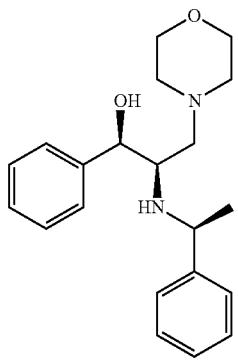

(1R, 2R)-2-((S)-1-phenylethylamino)-3-morpholino-1-phenylpropan-1-ol

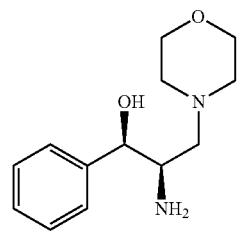

(1R, 2R)-2-amino-3-morpholino-1-phenylpropan-1-ol

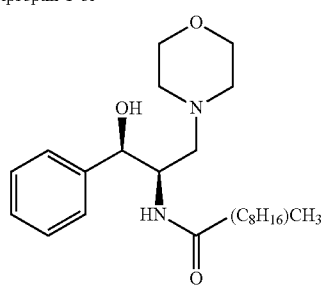

D-threo-PDMP

U.S. Pat. Nos. 5,945,442; 5,952,370; 6,030,995 and 6,051,598, which are all related to each other as being based on same or related disclosures, describe compounds which are structurally similar to the known compounds shown above.

A publication in Journal of Labelled Compounds & Radiopharmaceuticals (1996), 38(3), 285-97 discloses the compound of the formula

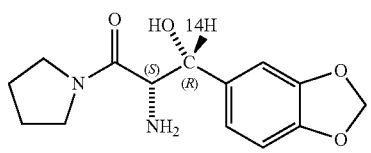

Published PCT application WO 01/38228 discloses

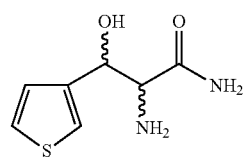 [SMILES: NC(=O)C(N)C(O)c1ccsc1]

in connection with a chromatographic method.

Kastron et al. in Latvijas PSR Zinatnu Akademijas Vestis, Kimijas Serija (1965) (4), 474-7 disclose the following compound.

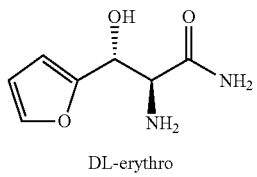 [SMILES: NC(=O)[C@@H](N)[C@@H](O)c1ccco1]

DL-erythro

SUMMARY OF THE INVENTION

The present invention is directed to methods of treating a patient suffering from one or more types of cognitive disorders using compounds of Formula 1

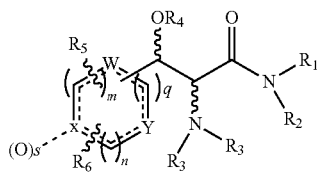

Formula 1 where $R_1$ is H or alkyl of 1 to 6 carbons,
$R_2$ is H, alkyl of 1 to 6 carbons or the $R_1$ and $R_2$ groups together with the nitrogen form a saturated or unsaturated 4, 5, 6 or 7 membered ring that optionally includes one or two heteroatoms independently selected from N, O and S, said 4, 5, 6 or 7 membered ring optionally being substituted with one or two COOH, $CH_2OH$, OH, $B(OH)_2$, cyano or halogen groups or with one or two alkyl groups having 1 to 6 carbons, or one or two carbons of said rings being attached to an oxygen to form keto groups and said 4, 5, 6 or 7 membered ring optionally being condensed with an aromatic or non-aromatic 5 or 6 membered ring that optionally includes 1 or heteroatoms selected from N, O and S;
$R_3$ is independently selected from H, alkyl of 1 to 20 carbons, cycloalkyl of 3 to 6 carbons, aryl or heteroaryl, aryl-alkyl, aryl-(hydroxy)alkyl, heteroaryl-alkyl or hetero-(hydroxy)alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons, or $R_3$ is $CO-R_7$, $SO_2R_7$ or $CO-O-R_7$ where $R_7$ is H, alkyl of 1 to 1 to 20 carbons, alkyl of 1 to 20 carbons substituted with and $NH_2$ group or with an NH—COalkyl group where the alkyl group has one to 6 carbons, aryl or heteroaryl, aryl-alkyl or heteroaryl-alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons;
$R_4$ is H, alkyl of 1 to 6 carbons or $CO-R_8$ where $R_8$ is alkyl of 1 to 6 carbons;
the wavy lines represent bonds connected to carbons having R or S configuration; the dashed lines represent a bond or absence of a bond with the proviso that the ring containing the dashed lines is aromatic;
m, n and q are integers independently selected from 0, 1, 2 or 3 with the proviso that the sum of m, n and q is 2 or 3;
s is zero (0) or when X is N then s is zero (0) or 1;
W, X and Y independently represent a CH, $CR_5$, $CR_6$ or a heteroatom selected independently of N, O and S, and $R_5$ and $R_6$ are independently selected from H, halogen, alkyl of 1 to 6 carbons, halogen substituted alkyl of 1 to 6 carbons, alkoxy of 1 to 6 carbons and thioxy of 1 to 6 carbons, phenyl, or $R_5$ and $R_6$ together with the atoms to which they are attached jointly form a carbocyclic or a heterocyclic ring, the carbocyclic ring having 5 or 6 atoms in the ring, the heterocyclic ring having 5 or 6 atoms in the ring and 1 to 3 heteroatoms independently selected from N, O and S;

said carbocyclic or heterocyclic ring jointly formed by $R_5$ and $R_6$ being optionally substituted with 1 to 6 $R_9$ groups where $R_9$ is independently selected from halogen, alkyl of 1 to 6 carbons, alkoxy of 1 to 6 carbons and thioxy of 1 to 6 carbons or a pharmaceutically acceptable salt of said compound with the proviso that Formula 1 does not cover compounds where $R_4$ is H, $R_1$ and $R_2$ jointly with the nitrogen form a pyrrolidino or morpholino ring, the sum of m, n and q is 3, and none of W, X and Y represent a heteroatom with the further proviso that the formula does not cover the compounds of the formula below:

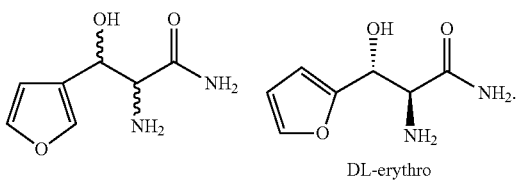

DL-erythro

The present invention is also directed to methods of treating cognitive disorders using the compounds of Formula 2

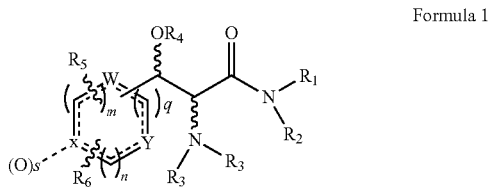

Formula 1 where $R_1$ is H or alkyl of 1 to 6 carbons,
$R_2$ is H, alkyl of 1 to 6 carbons or the $R_1$ and $R_2$ groups together with the nitrogen form a saturated or unsaturated 4, 5, 6 or 7 membered ring that optionally includes one or two heteroatoms independently selected from N, O and S, said 4, 5, 6 or 7 membered ring optionally being substituted with one or two COOH, $CH_2OH$, OH, $B(OH)_2$, cyano or halogen groups or with one or two alkyl groups having 1 to 6 carbons, or one or two carbons of said rings being attached to an oxygen to form keto groups and said 4, 5, 6 or 7 membered ring optionally being condensed with an aromatic or non-aromatic 5 or 6 membered ring that optionally includes 1 or heteroatoms selected from N, O and S;
$R_3$ is independently selected from H, alkyl of 1 to 20 carbons, cycloalkyl of 3 to 6 carbons, aryl or heteroaryl, aryl-alkyl, aryl-(hydroxy)alkyl, heteroaryl-alkyl or hetero-(hydroxy) alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons, or $R_3$ is CO—$R_7$, $SO_2R_7$ or CO—O—$R_7$ where $R_7$ is H, alkyl of 1 to 1 to 20 carbons, alkyl of 1 to 20 carbons substituted with an $NH_2$, $NHCOR_7$ or $NHCOOR_7$ group, aryl or heteroaryl, aryl-alkyl or heteroaryl-alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons;

the wavy lines represent bonds connected to carbons having R or S configuration;

the dashed lines represent a bond or absence of a bond with the proviso that the ring containing the dashed lines is aromatic;

$R_9$ and $R_{10}$ are independently H, alkyl of 1 to 6 carbons or $OR_{11}$, or $R_9$ and $R_{10}$ jointly represent $NOR_{11}$ with the proviso that when the dashed lines between carbons 2 and 3 of the propionic acid moiety represents a bond then $R_{10}$ does not exist and $R_9$ is not $OR_{11}$ with the further proviso that when $R_9$ is $OR_{11}$ then $R_{10}$ is not hydrogen;

$R_{11}$ is H, alkyl of 1 to 6 carbons or CO—$R_{12}$ where $R_{12}$ is alkyl of 1 to 6 carbons;

m, n and q are integers independently selected from 0, 1, 2 or 3 with the proviso that the sum of m, n and q is 2 or 3;

s is zero (0) or when X is N then s is zero (0) or 1;

W, X and Y independently represent a CH, $CR_5$, $CR_6$ or a heteroatom selected independently of N, O and S, and $R_5$ and $R_6$ are independently selected from H, halogen, alkyl of 1 to 6 carbons, halogen substituted alkyl of 1 to 6 carbons, alkoxy of 1 to 6 carbons and thioxy of 1 to 6 carbons, phenyl, or $R_5$ and $R_6$ together with the atoms to which they are attached jointly form a carbocyclic or a heterocyclic ring, the carbocyclic ring having 5 or 6 atoms in the ring, the heterocyclic ring having 5 or 6 atoms in the ring and 1 to 3 heteroatoms independently selected from N, O and S;

said carbocyclic or heterocyclic ring jointly formed by $R_5$ and $R_6$ being optionally substituted with 1 to 6 $R_9$ groups where $R_9$ is independently selected from halogen, alkyl of 1 to 6 carbons, alkoxy of 1 to 6 carbons and thioxy of 1 to 6 carbons or a pharmaceutically acceptable salt of said compound.

Any of the compounds described here may be used to treat a patient suffering from a cognitive disorder, such as an agnosia, an amnesia, an aphasia, an apraxia, a delirium, a dementia, and a learning disorder.

DETAILED DESCRIPTION OF THE INVENTION

Most compounds that are useful in the method of the invention contain one or more asymmetric centers, such that the compounds may exist in enantiomeric as well as in diastereomeric forms. In fact, most of the compounds of the present invention have two asymmetric carbons adjacent to one another and therefore can exist in erythro or threo form, with each of these two forms having dextrorotatory (D) or levorotary (L) enantiomers. Although the threo form is generally preferred in accordance with the present invention, unless it is specifically noted otherwise, the scope of the present invention includes all enantiomers, diastereomers and diastereomeric or racemic mixtures. In light of the foregoing, it should be clearly understood that the designation "DL" or "(+/−)" or "(±)" in this application includes the pure dextrorotatory enantiomer, the pure levorotatory enantiomer and all racemic mixtures, including mixtures where the two enantiomers are present in equal or in unequal proportions. Moreover, for simplicity sake in many of the structural formulas, such as in the example below, only one of the enantiomers is actually shown but when the designation "DL" or "(+/−)" or "(±)" appears it also includes the enantiomeric form (mirror image) of the structure actually shown in the formula.

For example:

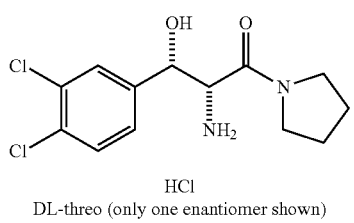 [SMILES: N[C@@H](C(=O)N1CCCC1)[C@@H](O)c1ccc(Cl)c(Cl)c1]

HCl
DL-threo (only one enantiomer shown)

Thus, in the example above, only one enantiomer is shown, but because the designation "DL" (or "(+/−)" or "(±)") appears below the formula, its optical isomer

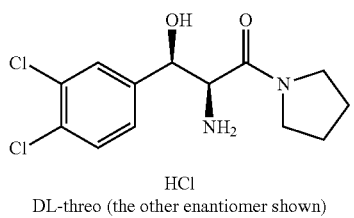 [SMILES: N[C@H](C(=O)N1CCCC1)[C@H](O)c1ccc(Cl)c(Cl)c1]

HCl
DL-threo (the other enantiomer shown)

and all racemic mixtures of the two optical isomers are also included.

In the case of some compounds of the present invention one enantiomer of the threo, and in some cases of the erythro, enantiomers is significantly more active than the other enantiomer of the same pair. For this reason the isolated enantiomer which is significantly more active than the other is considered a novel and inventive composition even if the racemic mixture or the other opposite enantiomer of the same compound have already been described in the prior art.

Some of the compounds that are useful in the method of the present invention contain three or more asymmetric centers. An example is the following compound Compound 214

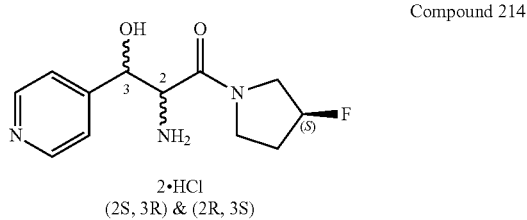

2·HCl
(2S, 3R) & (2R, 3S)

named Compound 214 in the description. The formula shown in the description for Compound 214 indicates two compounds of the threo isomer, but the two compounds indicated are not mirror images of each other, they are diastereomers. Another isomer pair is shown and described as Compound 215.

Compound 215

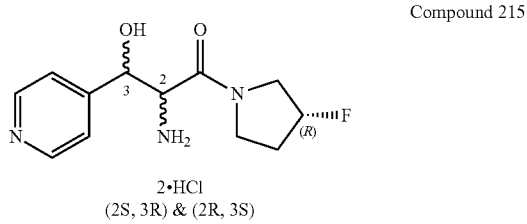

2·HCl
(2S, 3R) & (2R, 3S)

Keeping the foregoing examples in mind the reader one of ordinary skill in the art should readily understand the scope of each described example, although in a broad sense all isomers, enantiomers and racemic mixtures are within the scope of the invention.

The term "alkyl" in the general description and definition of the compounds includes straight chain as well as branch-chained alkyl groups.

Generally speaking the compounds of the invention may form salts with pharmaceutically acceptable acids or bases, and such pharmaceutically acceptable salts of the compounds of Formula 1 and of Formula 2 are also within the scope of the invention.

Referring now to the novel compounds of Formula 1, in a class of preferred compounds of the invention none of the W, X and Y groups is a heteroatom. Within this class, compounds are preferred where the sum of m, n and q is 3 and the aromatic group is unsubstituted or substituted with one or more halogen, alkyl of 1 to 6 carbons, or halogen substituted alkyl of 1 to 6 carbons. Compounds within this class are also preferred where the $R_5$ and $R_6$ groups form a carbocyclic ring, or a heterocyclic ring.

In another class of preferred compounds in accordance with Formula 1 one of the variables W, X and Y represents a heteroatom, preferably nitrogen and the sum of m, n and q is 3.

In still another class of preferred compounds in accordance with Formula 1 one or two of the variables W, X and Y represent a heteroatom, selected from N, O or S and the sum of m, n and q is 2.

Referring still to the compounds of Formula 1, compounds are preferred where $R_4$ is H or an acyl group, more preferably H.

With reference to the variables $R_3$, compounds in accordance with Formula 1 are preferred where both $R_3$ groups are H and where one $R_3$ group is H and the other is benzyl, monohalogeno, dihalogeno, methyl or methoxy substituted benzyl, cyclohexyl, an alkyl of 1 to 7 carbons, $COR_7$, $COOR_7$ where $R_7$ is alkyl of 1 to 15 carbons, benzyloxy, phenyl, methoxyphenyl, monohalogen or dihalogeno substituted phenyl, a 2-hydroxy-1-phenylethyl group or an alkyl group of 1 to 20 carbons itself substituted with an $NH_2$, $NHCOR_7$, or $NHCOOR_7$ group.

Referring now to the variables $R_1$ and $R_2$ in the compounds of Formula 1, compounds are preferred in accordance with the invention where $R_1$ and $R_2$ jointly form a pyrrolidine, a 3-fluoro or a 3,3-difluoro or an 3-hydroxy substituted pyrrolidine, a morpholine, a thiomorpholine, a piperazine, an alkyl substituted piperazine where the alkyl group has 1 to 6 carbons, an azetidine, a tetrahydrothiazole, an indoline, or a 2H-pyrrol ring or $R_1$ and $R_2$ are two alkyl groups of 1 to 3 carbons.

Referring now to the novel compounds of Formula 2, with respect to the variables W, X, Y, m, n, q, $R_1$, $R_2$, $R_5$, $R_6$, $R_3$ compounds are generally preferred in which these variables have the same preferences as in compounds of Formula 1.

With respect to $R_9$ and $R_{10}$, compounds are generally preferred where $R_9$ and $R_{10}$ are both hydrogen, where one of these two variables is hydroxy and the other is alkyl of 1 to 6 carbons, where the $R_9$ and $R_{10}$ groups jointly form an $NOR_{11}$ group, and where $R_9$ is hydrogen, the dashed line between carbons 2 and 3 represent a double bond and $R_{10}$ does not exist. With respect to $R_{11}$ compounds of Formula 2 are preferred where $R_{11}$ is H, or $COR_{12}$ where $R_{12}$ is alkyl of 1 to 3 carbons.

Presently still more preferred are Compounds of Formula 2 where $R_1$ and $R_2$ jointly with the nitrogen form a five-membered ring, where both $R_3$ groups are hydrogen and where one of the $R_3$ groups is hydrogen and the other is formyl.

Biological Activity, Modes of Administration

The compounds described here may be used to treat a patient suffering from one or more types of cognitive disorder, such as an agnosia, an amnesia, an aphasia, an apraxia, a delirium, a dementia, and a learning disorder.

To "treat," as used here, means to deal with medically. It includes, for example, administering a compound of the invention to prevent the onset of a cognitive disorder, to alleviate its severity, and to prevent its reoccurrence.

The term "cognitive disorder," as used here, means any condition characterized by a deficit in mental activities associated with thinking, learning, or memory. Examples of such disorders include agnosias, amnesias, aphasias, apraxias, deliriums, dementias, and learning disorders.

In some cases, the cause of a cognitive disorder may be unknown or uncertain. In other cases, the cognitive disorder may be associated with (that is, be caused by or occur in the presence of) other conditions characterized by damage to or loss of neurons or other structures involved in the transmission of signals between neurons. Hence, cognitive disorders may be associated with neurodegenerative diseases such as Alzheimer's disease, corticobasal degeneration, Creutzfeldt-Jacob disease, frontotemporal lobar degeneration, Huntington's disease, multiple sclerosis, normal pressure hydrocephalus, organic chronic brain syndrome, Parkinson's disease, Pick disease, progressive supranuclear palsy, or senile dementia (Alzheimer type); it may be associated with trauma to the brain, such as that caused by chronic subdural hematoma, concussion, intracerebral hemorrhage, or with other injury to the brain, such as that caused by infection (e.g., encephalitis, meningitis, septicemia) or drug intoxication or abuse.

Cognitive disorders may also be associated with other conditions which impair normal functioning of the central nervous system, including psychiatric disorders such as anxiety disorders, dissociative disorders, mood disorders, schizophrenia, and somatoform and factitious disorders; it may also be associated with conditions of the peripheral nervous system, such as chronic pain.

The compounds described here may be used to treat agnosias, amnesias, aphasias, apraxias, deliriums, dementias, learning disorders and other cognitive disorders regardless of whether their cause is known or not.

Examples of dementias which may be treated with the methods of the invention include AIDS dementia complex, Binswanger's disease, dementia with Lewy Bodies, frontotemporal dementia, multi-infarct dementia, Pick's disease, semantic dementia, senile dementia, and vascular dementia.

Examples of learning disorders which may be treated with the methods of the invention include Asperger's syndrome, attention deficit disorder, attention deficit hyperactivity disorder, autism, childhood disintegrative disorder, and Rett syndrome.

Examples of aphasia which may be treated with the methods of the invention include progressive non-fluent aphasia.

The compounds described here may also be used to treat patient having deficits in mental activities that are mild or that otherwise do not significantly interfere with daily life. Mild cognitive impairment is an example of such a condition: a patient with mild cognitive impairment displays symptoms of dementia (e.g., difficulties with language or memory) but the severity of these symptoms is such that a diagnosis of dementia may not be appropriate. The compounds described here may be used to treat mild cognitive impairment and other, similarly less severe forms of cognitive disorders.

Examples of Compounds of the Invention

Table 1, below, lists compounds which may be used in the method of the invention.

TABLE 1

Compounds for use in the method of the invention

| Compound or compound no. | Chemical Formula |
|---|---|
| L-threo-PDMP Available from Matreya, LLC | L-threo-PDMP structure |
| DL-erythro-PDMP Available from Matreya, LLC | DL-erythro-PDMP structure |
| D-threo-PDMP Available from Matreya, LLC | D-threo-PDMP structure |
| 1 | L-threo structure (HCl salt) |

TABLE 1-continued
Compounds for use in the method of the invention
| Compound or compound no. | Chemical Formula |
|---|---|
| 2 | 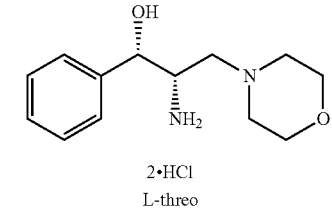 [SMILES: N[C@@H](CN1CCOCC1)[C@@H](O)c1ccccc1]<br>2·HCl<br>L-threo |
| 1:1 Racemic mixture | 2·HCl<br>L-threo |
| | 2·HCl<br>D-threo |
| 3 | 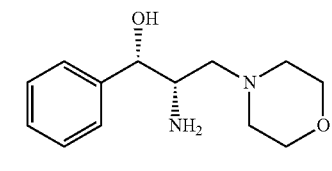<br>HCl<br>L-threo |
| 5 | 2·HCl<br>D-threo |
| 6 | 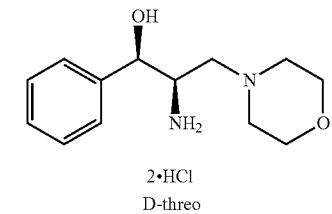 [SMILES: N[C@H](CN1CCOCC1)[C@H](O)c1ccccc1]<br>DL-threo |
| 7 | DL-threo |
| 9 | DL-threo |
| 15 | 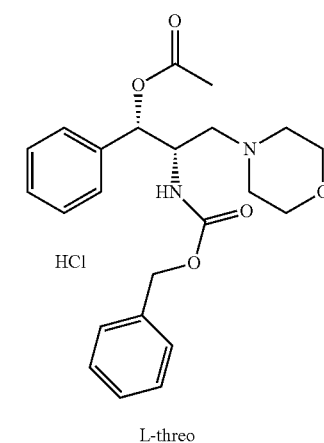<br>HCl<br>DL-threo |
| 16 | HCl<br>DL-threo |
| 17 | HCl<br>DL-threo |
| 20 | 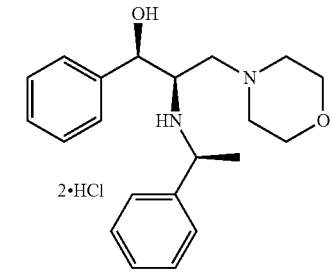<br>2·HCl<br>DL-threo |

TABLE 1-continued

Compounds for use in the method of the invention

| Compound or compound no. | Chemical Formula |
|---|---|
| 22 | 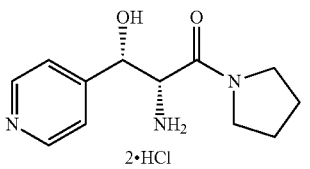<br>2·HCl<br>DL-threo |
| 23 | 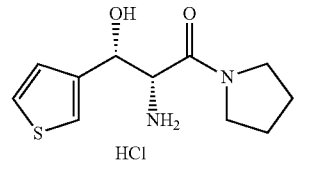<br>HCl<br>DL-threo |
| 24 | 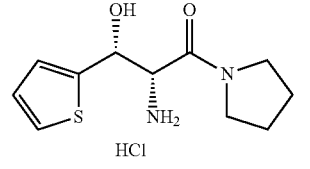<br>HCl<br>DL-threo |
| 26 | 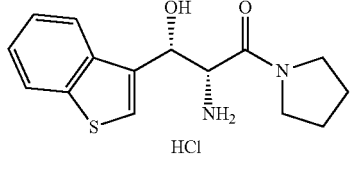<br>HCl<br>DL-threo |
| 27 | 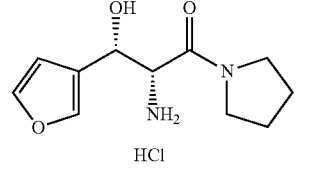<br>HCl<br>DL-threo |
| 28 | 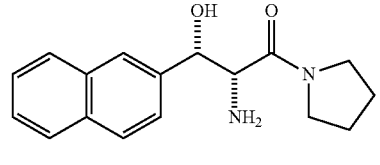<br>HCl<br>(+/-) |
| 29 | 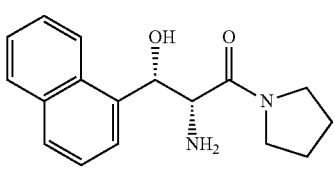<br>HCl<br>DL-threo |
| 30 | 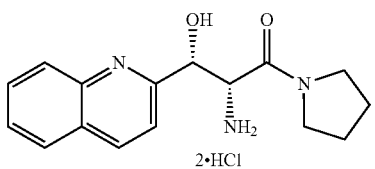<br>2·HCl<br>DL-threo |
| 34 | 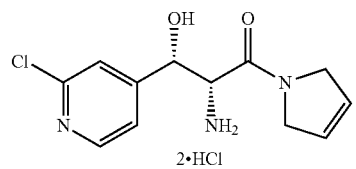<br>2·HCl<br>DL-threo |
| 35 | 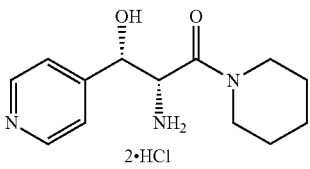<br>2·HCl<br>DL-threo |
| 40 | 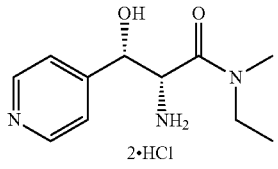<br>2·HCl<br>DL-threo |
| 41 | 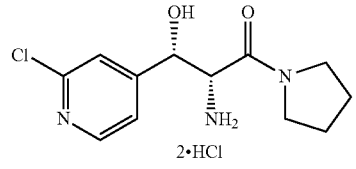<br>2·HCl<br>DL-threo |
| 43 | 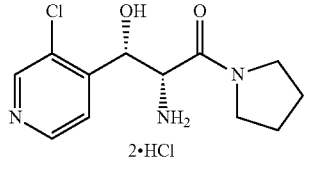<br>2·HCl<br>DL-threo |
| 46 | 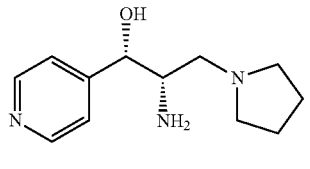<br>DL-threo |

TABLE 1-continued

Compounds for use in the method of the invention

| Compound or compound no. | Chemical Formula |
|---|---|
| 49 | 3-(2-oxo-1,2-dihydropyridin-3-yl) derivative with pyrrolidine amide, OH and NH₂ substituents (±) HCl |
| 49 | Same structure as above; HCl, DL-threo |
| 55 | 3-(pyridin-4-yl) derivative, N-benzoyl, pyrrolidine amide; HCl, DL-threo |
| 56 | 3-(pyridin-4-yl) derivative, N-(4-methoxybenzoyl), pyrrolidine amide; HCl, DL-threo |
| 57 | 3-(pyridin-4-yl) derivative, N-(3,4-dichlorobenzoyl), pyrrolidine amide; HCl, DL-threo |
| 58 | 3-(pyridin-4-yl) derivative, N-Cbz (benzyloxycarbonyl), pyrrolidine amide; HCl, DL-threo |
| 59 | 3-(pyridin-4-yl) derivative, N-nonanoyl (long alkyl chain acyl), pyrrolidine amide; HCl, DL-threo |
| 61 | 3-(pyridin-4-yl) derivative, N-methylamino, pyrrolidine amide; 2 HCl, DL-threo |
| 64 | 3-(pyridin-4-yl) derivative, N-hexyl (long alkyl chain amine), pyrrolidine amide; 2·HCl, DL-threo |

TABLE 1-continued
Compounds for use in the method of the invention
| Compound or compound no. | Chemical Formula |
|---|---|
| 67 | 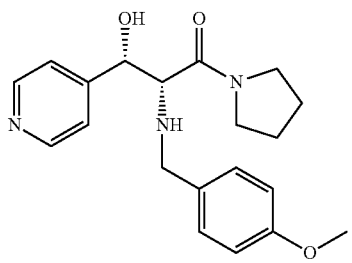<br>2·HCl<br>DL-threo |
| 68 | 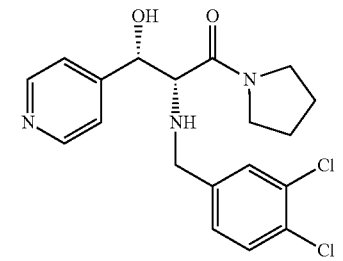<br>2·HCl<br>DL-threo |
| 69 | 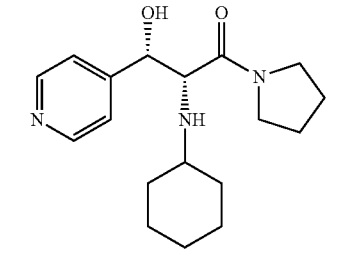<br>2·HCl<br>DL-threo |
| 203 | 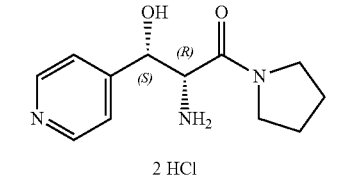<br>2 HCl<br>(−)-threo |
| 204 | 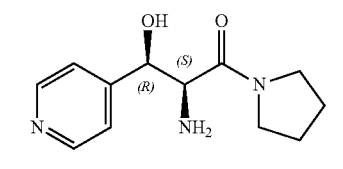<br>2 HCl<br>(+)-threo |
| 205 | 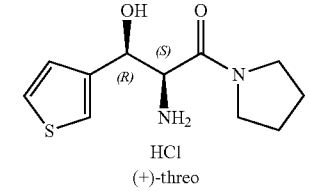<br>HCl<br>(+)-threo |
| 206 | 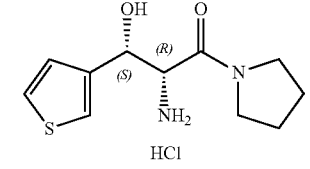<br>HCl<br>(−)-threo |
| 207 | 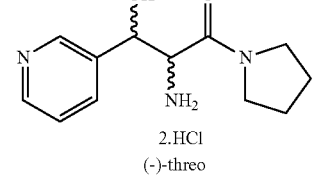<br>2.HCl<br>(−)-threo |
| 213 | 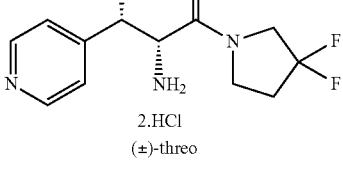<br>2.HCl<br>(±)-threo |
| 214 | 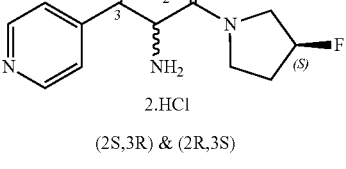<br>2.HCl<br>(2S,3R) & (2R,3S) |
| 215 | 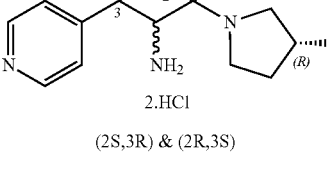<br>2.HCl<br>(2S,3R) & (2R,3S) |
| 216 | 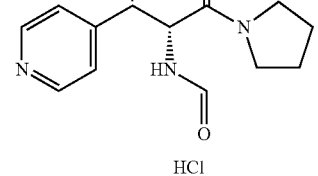<br>HCl<br>(±)-threo |

TABLE 1-continued

Compounds for use in the method of the invention

| Compound or compound no. | Chemical Formula |
|---|---|
| 219 | (pyridin-4-yl)-CH(OH)-CH(NH₂)-C(O)-N(pyrrolidine); 2.HCl; (±)-erythro |
| 224 | (pyridin-4-yl)-C(=NOH)-CH(NH₂)-C(O)-N(pyrrolidine); 2.HCl; (±) |
| 226 | (pyridin-4-yl)-CH(OH)-CH(NH-CH₂-(2-iodophenyl))-C(O)-N(pyrrolidine); 2.HCl; (±)-threo |
| 227 | (pyridin-4-yl)-CH(OH)-CH(NH-CH₂-(3-iodophenyl))-C(O)-N(pyrrolidine); 2.HCl; (±)-threo |
| 228 | (pyridin-4-yl)-(R)CH(OH)-(S)CH(NH-CH₂-(3-iodophenyl))-C(O)-N(pyrrolidine); 2 HCl |
| 229 | (pyridin-4-yl)-(R)CH(OH)-(S)CH(NH-CH₂-(3-iodophenyl))-C(O)-N(pyrrolidine); 2 HCl |
| 230 | (thiophen-3-yl)-CH(OH)-CH(NH₂)-C(O)-N(morpholine); HCl; (±)-threo |
| 232 | (pyridin-3-yl)-CH(OH)-CH(NH₂)-C(O)-N(morpholine); 2.HCl; (±)-threo |
| 234 | (pyridin-4-yl)-(S)CH(OH)-(R)CH(NH-(R)CH(CH₂OH)(phenyl))-C(O)-N(pyrrolidine); 2 HCl |
| 236 | (pyridin-4-yl)-CH₂-(R)CH(NH₂)-C(O)-N(pyrrolidine); 2 HCl |

TABLE 1-continued

Compounds for use in the method of the invention

| Compound or compound no. | Chemical Formula |
|---|---|
| 238 | (structure: pyridine-CH(OH)-CH(NHC(O)(CH2)4NH2)-C(O)-N-pyrrolidine) (±)-threo |
| 240 | (structure: 4-pyridyl-CH2-CH(S)(NH2)-C(O)-N-pyrrolidine) 2 HCl |
| 247 | (structure: pyridine-CH(S)(OH)-CH(R)(NH2)-C(O)-N-pyrrolidine-(R)-OH) 2.HCl<br>+<br>(structure: pyridine-CH(R)(OH)-CH(S)(NH2)-C(O)-N-pyrrolidine-(R)-OH) 2.HCl |
| 248 | (structure: pyridine-CH(OH)-CH(NH2)-C(O)-N-pyrrolidine-(S)-F) 2.HCl (−)-threo |
| 255 | (structure: 3-pyridyl-CH(S)(OH)-CH(R)(NH2)-C(O)-N-pyrrolidine-(S)-F) 2.HCl<br>+<br>(structure: 3-pyridyl-CH(R)(OH)-CH(S)(NH2)-C(O)-N-pyrrolidine-(S)-OH) 2.HCl |
| 256 | (structure: 3-thienyl-CH(S)(OH)-CH(R)(NH2)-C(O)-N-pyrrolidine-(S)-F) 2.HCl<br>+<br>(structure: 3-thienyl-CH(R)(OH)-CH(S)(NH2)-C(O)-N-pyrrolidine-(S)-F) 2.HCl |

Any of the foregoing compounds, in addition to the compounds described below, can be used in the methods of the invention to treat any cognitive disorder.

Modes of Administration:

The compounds of the invention may be administered at pharmaceutically effective dosages. Such dosages are normally the minimum dose necessary to achieve the desired therapeutic effect; in the treatment of cognitive disorders, the desired therapeutic effect is an improvement in cognitive functioning, or an alleviation of any of the symptoms associated with agnosia, amnesia, aphasia, apraxia, delirium, dementia, or learning disorders. For human adults such doses generally will be in the range of 0.1-5,000 mg/day; more preferably in the range of 1 to 3,000 mg/day, 10 mg to 500 mg/day, 500 to 1,000 mg/day, 1,000 to 1,500 mg/day, 1,500 to 2,000 mg/day, 2,000 to 2,500 mg/day, or 2,500 to 3,000 mg/day. However, the actual amount of the compound to be administered in any given case will be determined by a physician taking into account the relevant circumstances, such as the severity of the cognitive disorder, the age and weight of the patient, the patient's general physical condition, the cause of the disorder, and the route of administration.

The compounds are useful in the treatment of cognitive disorders in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, intraperitonial, parenteral, subcutaneous, intranasal, intrathecal, intramuscular, intravenous and intrarectal modes of delivery. Compositions useful in the method of the invention may further include an excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

EXAMPLES

The inventors demonstrated memory-enhancing activity with three compounds of the invention. The passive avoidance task exploits the tendency for rodents to avoid environments previously associated with an aversive stimulus (e.g. shock) and is therefore a reliable measure of emotional memory. The Morris water maze (MWM) task, a test of spatial learning and memory, requires that the animal learns the spatial locations of various extra-maze cues in order to accurately locate an escape platform that is hidden beneath the surface of the water in a water tank. In all of these tasks, the tested compounds improved memory: in passive avoidance, this was true for young mice, and in the MWM task, the compounds significantly improved learning and memory in aged rats.

Importantly, the tested compounds are orally active, and therefore could be administered in many forms, including but not limited to tablet or capsule. These compounds may also be administered IV, intramuscularly, intrathecally, subcutaneously, or intraperitoneally.

Table 2, below, indicates the effects of compounds of the invention in a passive avoidance task (latency to enter the dark/shock compartment as dependent variable). Data were analyzed with One-Way ANOVAs followed by Bonferroni-corrected post-hoc measures (required P value dependent upon number of comparisons). The table below includes data from Vehicle-treated mice and mice treated with Compound A and Compound B.

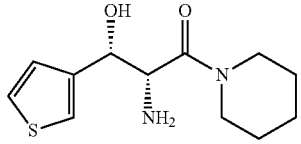

Compound A

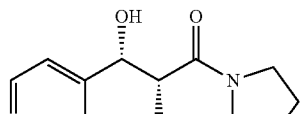

Compound B

All treatments were administered IP immediately post-training. There were no significant differences during training (pre-treatment), but the post-training injections of Compound A and Compound B significantly improved memory for the shock-associated environment.

| | Dose (mg/kg) | Training latency Day 0 | Testing latency Day 1 | | Day 4 | Day 7 |
|---|---|---|---|---|---|---|
| Vehicle | | 8.51 ± 0.95 | 33.49 ± 8.53 | | 36.15 ± 12.25 | 9.82 ± 1.93 |
| A | 1 | 14.26 ± 2.85 | 64.34 ± 14.21 * | | 65.52 ± 26.20 | 54.32 ± 25.75 * |
| | 10 | 9.88 ± 1.52 | 82.58 ± 17.18 * | | 58.33 ± 9.49 * | 47.87 ± 22.67 * |
| B | 1 | 6.58 ± 1.01 | 95.42 ± 24.99 ** | | 81 ± 26.81 * | 43.55 ± 19.01 * |
| | 10 | 8.43 ± 2.50 | 126.27 ± 15.64 ** | | 83.4 ± 20.11 * | 56.22 ± 19.62 ** |

Overall effects of treatment were determined by repeated measures ANOVA. Post-hoc Bonferroni tests identified differences between individual treatment groups relative to control:
* Indicates P < 0.02 relative to vehicle,
** indicates P < 0.01 relative to vehicle.
N = 6/group.

Table 3, below, indicates the effects of Compound C in the Morris water maze task (mean escape latencies across testing days are shown).

Compound C

Data were analyzed with a Mann-Whitney U Test. Mean escape latency indicates the group mean over three sessions to escape onto the hidden platform. Data are shown for days 7-11 (the water maze training days); animals were dosed twice daily (PO) with 10 mg/kg Compound No. 1 or vehicle (as indicated) on Days 1-6 prior to water maze training.

| | | Mean Escape Latency (sec) | | | | |
|---|---|---|---|---|---|---|
| Group | Treatment | Day 7 | Day 8 | Day 9 | Day 10 | Day 11 |
| Young rats | Vehicle | 70.3 ± 3.5 | 40.2 ± 13.3 | 23.2 ± 1.7 | 22.0 ± 4.2 | 19.9 ± 6.2 |
| Aged rats | Vehicle | 70.7 ± 2.2 | 47.6 ± 3.7 | 53.7 ± 4.0 ** | 35.7 ± 0.6 * | 41.3 ± 4.5 ** |
| Aged rats | Compound C | 69.9 ± 4.0 | 49.3 ± 5.4 | 41.0 ± 1.8 * ◊ | 28.0 ± 2.2 | 30.4 ± 3.4 |

Young and aged controls decreased their escape latencies (time to find the platform) from session to session, indicating that they could learn to locate the hidden platform. Aged controls had longer escape latencies and path length than young controls during water-maze training, suggesting age-related learning deficits. The effect of age was mainly observed during the $3^{rd}$-$5^{th}$ training days (Day 9-11). An analysis of variance conducted in control animals supported a statistically significant main effect of age over the training period (ANOVA: $F_{Age}$ (all trials)=15.644; $p<0.001$).

No clear effects were observed in aged controls on average speed as compared with young controls (data not shown), suggesting the absence of motor impairment in aged rats.

Compound C (10 mg/kg), administered twice daily for 6 days prior to the experiment and twice daily during the experiment, decreased the escape latency of aged rats over the training period, as compared with aged controls. The effect of Compound C was statistically significant when pooling the data obtained during the last 3 training sessions. Compound C did not affect the average speed, as compared with aged controls (data not shown).

*=$p<0.05$; **=$p<0.01$ (aged controls versus young controls).
◊ =$P<0.05$ (aged rats treated with Compound C versus young controls).

Materials and Methods
Passive Inhibitory Avoidance
Animals

C57B/6 male mice (20-25 g; n=6-8/group) were used in this study.

Training/Testing

One Day 0, animals were individually placed in the bright side of a 2-chambered inhibitory avoidance box. Mice were given 35 seconds to acclimate after which a door between the two compartments was lifted and the animals were allowed to cross over into the dark compartment. Once they crossed over, the gate would close and the animal would receive a mild (0.15 mA, 2 sec) footshock. Memory retention for the shock-associated environment was evaluated 24 hours (Day 1), 4 (Day 4) and 7 (Day 7) days later. On each of the three memory retention tests (Days 1, 4, and 7), the mouse was given 15 seconds to acclimate before the gate was lifted. Latency to enter the dark (shock) compartment was measured and considered an index of passive fear avoidance. Maximum trial length=180 sec.

Morris Water Maze

The Morris Maze consisted of a circular water tank (150 cm in diameter) filled with water and maintained at 27° C. with an escape platform (15 cm in diameter) 18 cm from the perimeter always in the same position 2 cm beneath the surface of the water. The water was made opaque by addition of a non-toxic coloring agent rendering the platform invisible. The testing was performed under light of moderate intensity.

The animals were given 5 training sessions over 5 consecutive days. Each training session consisted of 3 consecutive trials in the Morris Maze separated by 120 seconds. For each trial the animal was placed in the maze at one of two starting points equidistant from the escape platform and allowed to find the escape platform. The animal was left on the escape platform for 60 seconds followed by a 60-second rest in an individual cage before starting a new trial. If the animal did not find the platform within 120 seconds, the experimenter removed it from the water and placed it on the platform for 60 seconds. During the 3 trials the animals started the maze from the different starting points in a randomly determined order per animal.

The trials were video-recorded and the behavior of the animals was analyzed using a video-tracking system (Panlab: Smart). The principal measure taken was the escape latency (time to find the hidden platform) at each trial. Additional measures (path length (distance traveled to find the hidden platform) and average speed) were also measured.

Aged animals show amnesia in this task as indicated by a lower capacity to reduce their escape latencies from trial to trial.

15 aged rats were studied per group. The experiment also included a young control group. The test was performed blind.

Compound C was evaluated at the dose of 10 mg/kg, administered p.o., and compared with a vehicle control group. The animals received the assigned treatment twice daily for 6 days prior to water-maze training. Twice daily administration continued during training, with one administration 60 minutes before each training session and the second administration between either 8.30-9.30 am or 4:30-5:30 pm, whichever was furthest from the training session for that particular animal.

The experiment therefore included 3 groups.

Data were analyzed by comparing treated groups with aged control using Mann Whitney U tests. In addition, the data were submitted to a two-factor analysis of variance (with age and session as factors, with repeated measures for session).

Synthetic Methods for Obtaining the Compounds of the Invention, Experimental

U.S. Patent Application Nos. 60/647,271 (WO/2006/081273; WO/2006/081280; WO/2006/081252 and WO/2006/081276), the disclosure of which is incorporated by reference herein, discloses additional compounds which may be utilized in the method of the present invention, and discloses methods for their synthesis.

What is claimed is:

1. A method for treating a cognitive disorder, the method comprising administering to a patient in need of such treatment a therapeutically effective amount of a compound of the following structure:

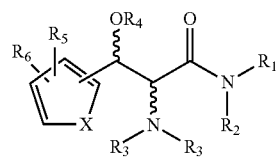

or an enantiomer, diastereomer, or pharmaceutically acceptable salt thereof, wherein:

X is O or S;

$R_1$ is H or alkyl of 1 to 6 carbons, $R_2$ is H, alkyl of 1 to 6 carbons or the $R_1$ and $R_2$ groups together with the nitrogen form a saturated or unsaturated 5 or 6 membered ring that optionally includes one or two heteroatoms independently selected from N, O and S, said 4, 5, 6 or 7 membered ring optionally being substituted with one or two COOH, $CH_2OH$, OH, $B(OH)_2$, halogen groups or cyano groups with one or two alkyl groups having 1 to 6 carbons, $R_3$ is H, CO—$R_7$ or CO—O—$R_7$ where $R_7$ is H, alkyl of 1 to 1 to 20 carbons, aryl or heteroaryl, aryl-alkyl, aryl (hydroxy)alkyl, heteroaryl-alkyl or heteroaryl(hydroxy) alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 3 carbons;

R₄ is H, alkyl of 1 to 6 carbons, or CO—R₈ where R₈ is alkyl of 1 to 6 carbons;

R₅ and R₆ are independently selected from H, halogen, alkyl of 1 to 6 carbons, alkoxy of 1 to 6 carbons and thioxy of 1 to 3 carbons, or R₅ and R₆ together with the atoms to which they are attached jointly form a carbocyclic or a heterocyclic ring, the carbocyclic ring having 5 or 6 atoms in the ring, the heterocyclic ring having 5 or 6 atoms in the ring and 1 to 3 heteroatoms independently selected from N, O and S;

said carbocyclic or heterocyclic ring jointly formed by R₅ and R₆ being optionally substituted with 1 to 6 R₉ groups where R₉ is independently selected from halogen, alkyl of 1 to 6 carbons, alkoxy of 1 to 6 carbons, and the wavy lines represent bonds connected to carbons having R or S configuration, with the proviso that the claim does not cover the compound shown below

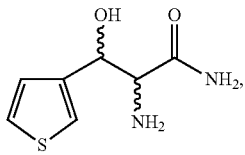 [SMILES: NC(=O)C(N)C(O)c1ccsc1]

and wherein the cognitive disorder is associated with a neurodegenerative disease selected from the group consisting of Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, and senile dementia (Alzheimer type).

2. The method of claim 1, wherein the compound has the following structure:

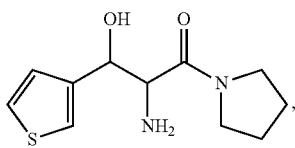 [SMILES: NC(C(=O)N1CCCC1)C(O)c1ccsc1]

or an enantiomer, diastereomer, or pharmaceutically acceptable salt thereof.

3. The method of claim 2, wherein the compound is (2S, 3S)-2-amino-3-hydroxy-1-(pyrrolidin-1-yl)-3-(thiophen-3-yl)propan-1-one, or pharmaceutically acceptable salt thereof.

4. The method of claim 2, wherein the compound is (2S, 3R)-2-amino-3-hydroxy-1-(pyrrolidin-1-yl)-3-(thiophen-3-yl)propan-1-one, or pharmaceutically acceptable salt thereof.

5. The method of claim 2, wherein the compound is (2R, 3S)-2-amino-3-hydroxy-1-(pyrrolidin-1-yl)-3-(thiophen-3-yl)propan-1-one, or pharmaceutically acceptable salt thereof.

6. The method of claim 2, wherein the compound is (2R, 3R)-2-amino-3-hydroxy-1-(pyrrolidin-1-yl)-3-(thiophen-3-yl)propan-1-one, or pharmaceutically acceptable salt thereof.

7. The method of claim 1, wherein the compound has the following structure

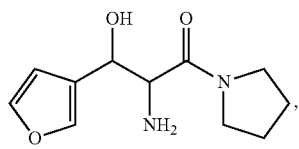 [SMILES: NC(C(=O)N1CCCC1)C(O)c1ccoc1]

or an enantiomer, diastereomer, or pharmaceutically acceptable salt thereof.

8. The method of claim 7, wherein the compound is (2S, 3S)-2-amino-3-(furan-3-yl)-3-hydroxy-1-(pyrrolidin-1-yl)propan-1-one, or pharmaceutically acceptable salt thereof.

9. The method of claim 7, wherein the compound is (2S, 3R)-2-amino-3-(furan-3-yl)-3-hydroxy-1-(pyrrolidin-1-yl)propan-1-one, or pharmaceutically acceptable salt thereof.

10. The method of claim 7, wherein the compound is (2R, 3S)-2-amino-3-(furan-3-yl)-3-hydroxy-1-(pyrrolidin-1-yl)propan-1-one, or pharmaceutically acceptable salt thereof.

11. The method of claim 7, wherein the compound is (2R, 3R)-2-amino-3-(furan-3-yl)-3-hydroxy-1-(pyrrolidin-1-yl)propan-1-one, or pharmaceutically acceptable salt thereof.

* * * * *